United States Patent [19]

Rico

[11] 4,443,196

[45] Apr. 17, 1984

[54] TOOTH ROOT EXTRACTOR

[76] Inventor: Miguel Rico, 3406 W. 43th St., Shawnee Mission, Kans. 66205

[21] Appl. No.: 420,308

[22] Filed: Sep. 20, 1982

[51] Int. Cl.³ .............................................. A61C 3/00
[52] U.S. Cl. ................................................. 433/158
[58] Field of Search ................ 433/157, 158, 161, 152

[56] References Cited

U.S. PATENT DOCUMENTS

| | | |
|---|---|---|
| 748,098 | 3/1905 | Beazley . |
| 1,094,269 | 4/1914 | Taylor .................................. 433/157 |
| 1,102,850 | 7/1914 | Arden . |
| 2,210,349 | 8/1940 | Van Beeck . |

Primary Examiner—Robert Peshock
Attorney, Agent, or Firm—Litman, Day & McMahon

[57] ABSTRACT

A tooth root extractor comprises first and second elongate arms pivotally connected at adjacent first ends thereof. A threaded tooth root screw is operably retained by a free end of the first arm and operably engages and is received within a root of a tooth to be extracted. A free end of the second arm is supported by gums or teeth surrounding the tooth root. A jackscrew positioned between the two arms is manipulable to bias the arms apart, thereby extracting the tooth root. The jackscrew is located exteriorly of the mouth of the patient when the extractor is in an operational position thereof.

11 Claims, 7 Drawing Figures

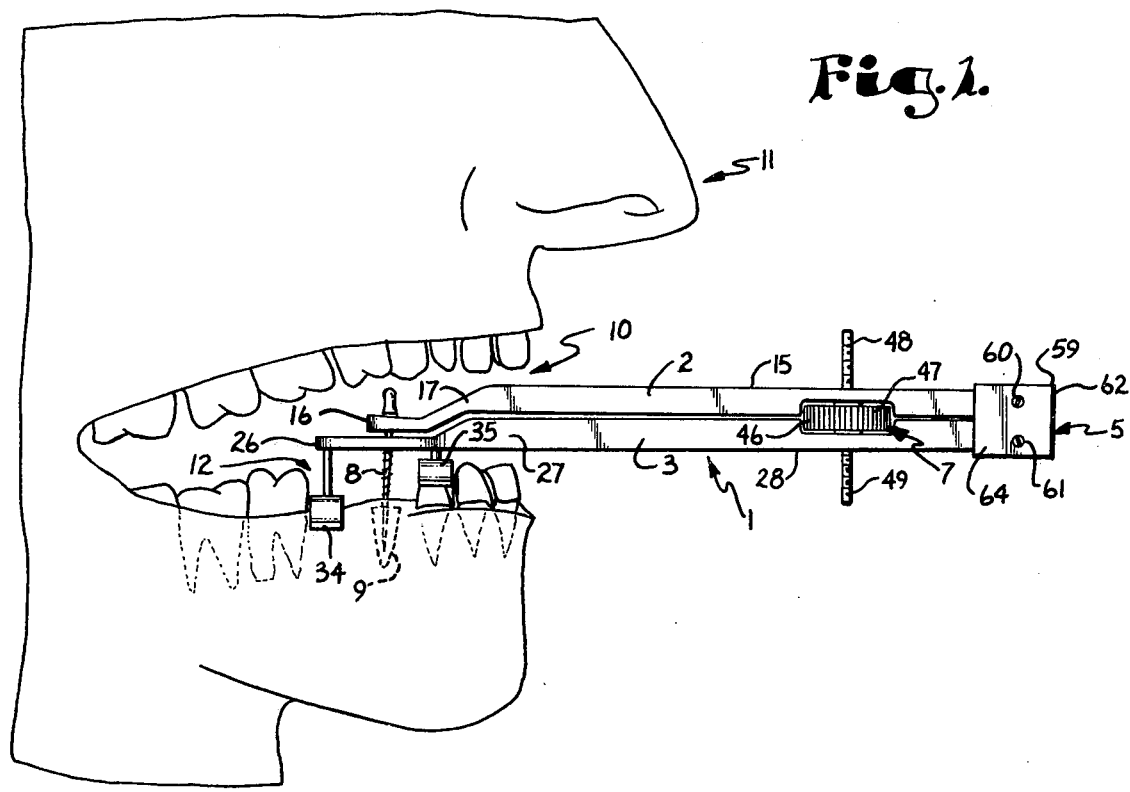
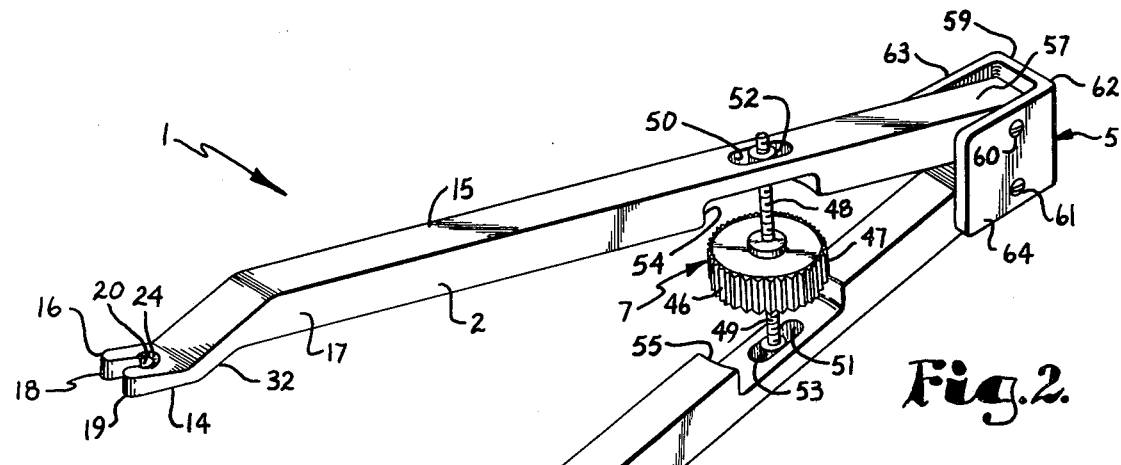

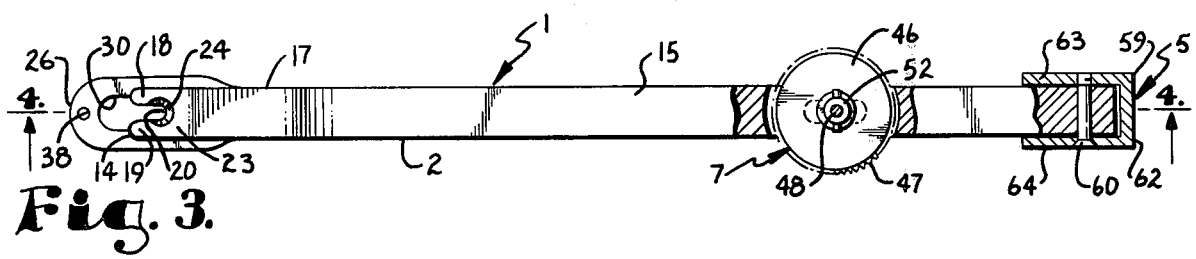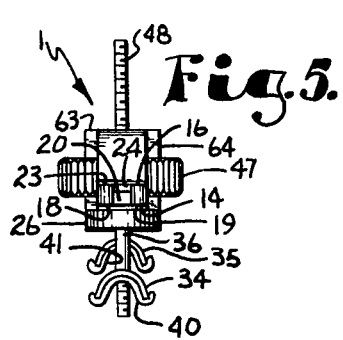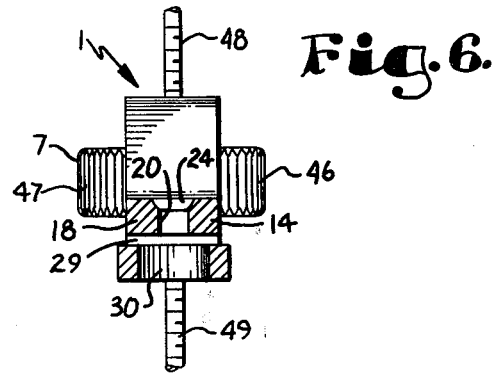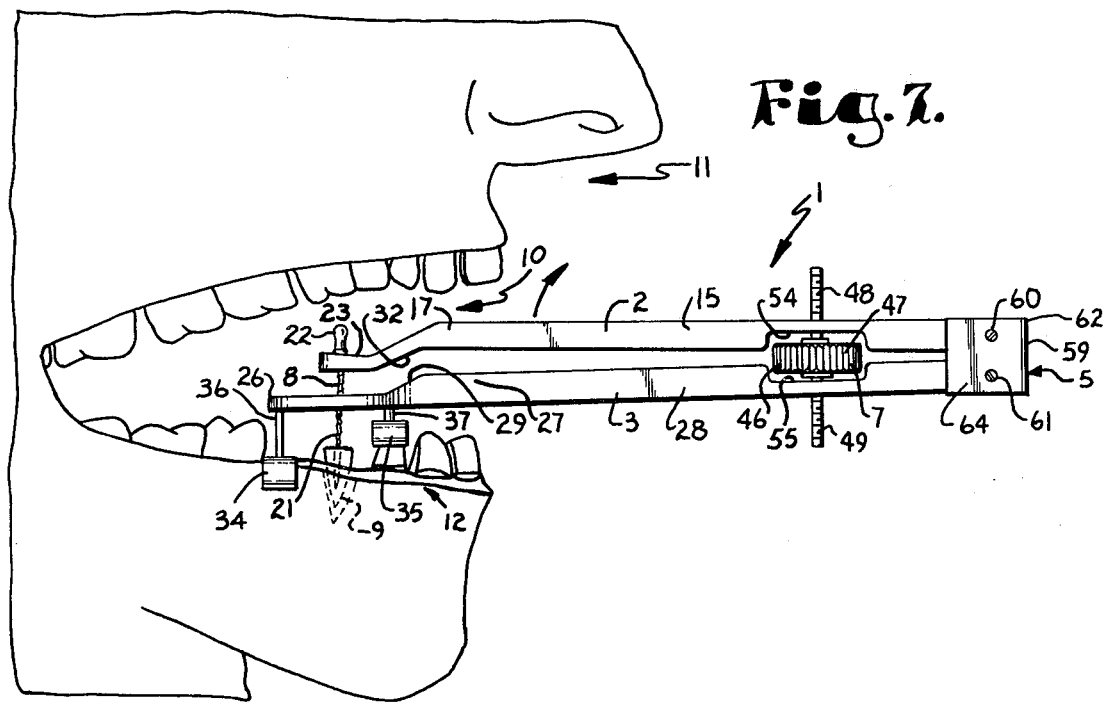

TOOTH ROOT EXTRACTOR

BACKGROUND OF THE INVENTION

This invention relates to dental devices and in particular to such devices utilized in the extraction of tooth roots.

Dentists are often required to remove a tooth root of a patient after the root has become diseased or damaged, especially when a tooth has been broken off due to injury or during attempted extraction. Once the tooth crown breaks off so that only the root below the gum line remains, it is very difficult to remove the remaining root with standard dental extraction forceps. When a tooth breaks leaving only the root, the standard procedure used by dentists involves cutting the surrounding gum tissue, cutting and removing part of the bone around the tooth root, and subsequently prying the tooth root out of the patient's jaw. This standard procedure is painful, produces substantial trauma in the mouth region surrounding the root, is very time consuming and the resulting damaged tissue is slow in healing. This standard procedure does not provide for a controlled, stable extraction due to the amount of hand prying involved.

There are specially designed root extraction instruments in the prior art. However, such instruments are often cumbersome and difficult to operate, since such instruments are typically wholly placed within the mouth of a patient such that manipulation must take place entirely within the mouth and the mouth of the patient must be opened at painful angles to accommodate the instruments. Certain of these devices employ the use of a tooth root screw which is threadably inserted in the tooth root. Some of the prior art devices utilize sliding tubes, one of which tubes is connected to a tooth root screw and the other is supported by the teeth of the patient; however, pulling on handles connected to the tubes requires work inside the mouth and the device tends to be hard to stabilize. Other devices urge the tooth root from the jaw by means of a tooth root screw which has oppositely threaded root and shank portions and which is adapted to have the root portion screwed into a root canal of a root to be removed. A nut is screwed onto the shank portion, engages a base plate supported by the teeth, and is turned by hand or with a wrench until the tooth root is freed from the jaw. These latter devices have apparently not been heavily utilized by the dental community because of the awkwardness of using these devices, since manual manipulation of the moving parts thereof is required almost entirely within the limited confines of the mouth. Use of prior art devices is especially difficult when extracting rearward tooth roots due to the reduced vertical space available in the rear of the mouth even when wide open. The later discussed devices also require substantial mechanical adjustment in the tooth root screw engaging process and do not use force-absorbing dental saddles which easily adjust to accommodate varied tooth and gum regions to allow a stable extraction of the tooth root which does no damage to surrounding teeth and gums.

Thus, there exists a need for a dental device which provides for the extraction of tooth roots with minimal amounts of trauma to the surrounding tissue and requires minimal healing time, maintains a relatively low profile within the mouth, provides for quick and easy engagement of a root screw imbedded in a root by a remainder of the dental device, can be manipulated and operated externally of the mouth, and which takes advantage of leverage and purchase principles to ease extraction.

OBJECTS OF THE INVENTION

The principal objects of the present invention are: to provide a dental device for extracting tooth roots; to provide such a dental device which utilizes leverage and purchase principles to facilitate extraction of such a tooth root; to provide such a dental device which may be functionally manipulated outside of the patient's mouth; to provide such a dental device which simply and expeditiously engages a tooth root screw without extensive mechanical adjustment; to provide such a dental device which has low profile arm members which allow extraction without requiring forcible extension of the jaws of a patient; to provide such a dental device which produces little or no tissue damage or trauma in the patient and which will leave a tooth socket which will have a tendency to heal sooner than when a surgical procedure is utilized; to provide such a dental device which will have force-absorbing, adjustable dental saddles to allow biasing against the teeth or gums without damage thereto; and to provide such a dental device which is relatively simple to use, economical to manufacture, and particularly well adapted for the proposed usage thereof.

Other objects and advantages of this invention will become apparent from the following description taken in conjunction with the accompanying drawings wherein are set forth, by way of illustration and example, certain embodiments of this invention.

SUMMARY OF THE INVENTION

A dental device is provided to effect the extraction of tooth roots. The device has two elongate arm members interconnected together, preferably by hinge means. The first arm has holding means positioned thereon which are spaced from said hinge means and which operably retain a tooth root screw. The second arm member is longitudinally aligned with the first arm member in a mating configuration.

The first end of the second arm is generally oval-shaped with an elongate oval eyelet therein. The eyelet allows the screw to pass therethrough so that the holding means can receive the screw.

A pair of adjustable, cushioned dental saddles are connected to the first end of the second arm. The saddles engage the tooth and gum region adjacent to the tooth root to be extracted. The saddles resiliently absorb and cushion the force exerted by the device during the extraction.

The arm members are selectively urged apart by manipulative spreader means which means are substantially spaced horizontally from the root screw. Such placement provides a leverage effect at the respective first ends of the arms by utilizing the hinge means as a fulcrum, and allows the spreader means to be positioned and manipulated externally of the mouth of the patient.

The drawings constitute a part of this specification and include exemplary embodiments of the present invention and illustrate various objects and features thereof.

BRIEF DESCRIPTION OF THE DRAWINGS

FIG. 1 is a side elevational view of a tooth root extractor embodying the present invention positioned within a mouth and shown in a closed position thereof.

FIG. 2 is an enlarged perspective view of the tooth root extractor having arms wherein the arms are spread in an exaggerated manner to show detail thereof.

FIG. 3 is an enlarged top plan view of the tooth root extractor with portions broken away to reveal detail thereof.

FIG. 4 is an enlarged cross-sectional view of the tooth root extractor taken along line 4—4 FIG. 3.

FIG. 5 is an enlarged front elevational view of the tooth root extractor.

FIG. 6 is a further enlarged cross-sectional view of the tooth root extractor taken along line 6—6 of FIG. 4.

FIG. 7 is a side elevational view of the tooth root extractor, similar to FIG. 1, positioned within the mouth and shown in an open position thereof.

DETAILED DESCRIPTION OF THE PREFERRED EMBODIMENT

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally indicates a dental device or tooth root extractor embodying the present invention. The tooth root extractor 1 comprises a first arm member 2 and a second arm member 3 pivotally connected by hinge means, such as a hinge 5. Spreader means, such as a jackscrew 7 as seen in the illustrated embodiment, a turnbuckle or the like are utilized to apply opposing force to the arm members 2 and 3 and to thereby selectively manipulate the first and second arm members 2 and 3 so as to pivot with respect to one another about the hinge 5. A tooth root screw 8 is operably received by the first arm member 2 at a location therealong spaced from both the hinge 5 and the jackscrew 7. The screw 8 is manipulated to be secured in a tooth root 9 within an oral cavity structure or mouth 10 of a patient 11.

The extractor 1 has an operative position wherein portions of the arm members 2 and 3 extend into the mouth 10 and preferably wherein the hinge 5 and jackscrew 7 are exterior of the mouth 10, as seen in FIG. 1. When the extractor 1 is in the operative position thereof, the second arm member 3 has a pre-extraction position wherein such arm member 3 is supported by a tooth and gum region 12 adjacent to the tooth root 9 to be extracted. The first arm member 2 is positioned almost parallel to and adjacent the second arm member 3, when the extractor 1 is in the operative position thereof, and has engaging or holding means, such as a forked terminus 14, which receive the screw 8. The jackscrew 7 selectively pivots the first arm member 2 at the hinge 5 with respect to the second arm member 3. During extraction of a tooth root 9 the second arm member 3 remains in relatively stationary and stable contact with the tooth and gum region 12.

The screw 8 is operably embedded, normally by manual rotation of the screw 8, into a root canal associated with a tooth root 9 and is aligned so as to preferably have a generally vertical axis. The screw 8 may be any dental device, such as a root canal file or a specially made screw, having a relatively small diameter so as to fit into a normal root canal of patient 11. The screw 8 has reverse threads, flighting or the like at a lower end for securely holding the root screw 8 in the canal of the tooth root 9 after insertion thereinto. Various suitable root files and screws are well known to those practicing in the art. It is foreseen that the tooth root 9 may be in a position such that the screw 8 must be secured therein at an angle varying from vertical but the normal position will be vertical. The screw 8 may be of variable size depending upon the condition, size, and placement of the tooth root 9 and the particular patient 11.

The first arm member 2 is elongate and has an operative position in which a distal, free or first end 16 associated with the forked terminus 14 and an internal portion 17 of the first arm member 2 associated therewith are located within the mouth 10, and substantially all of a remainder or external portion 15 of the first arm member 2 is located outside the mouth 10. In the operative position, the first arm member 2 is preferably substantially perpendicularly aligned relative to the screw axis 8. The the root screw 8 is received and held by the forked terminus 14 of the first arm 2. In the present embodiment, the forked terminus 14 has rounded and generally parallel screw supporting tips 18 and 19. At an inner junction of the tips 18 and 19 is a semicircular notch 20 which has an upper chamfered or beveled edge 24.

The screw 8 includes a threaded portion 21 and a handle portion 22 which is greater in diameter than the notch 20 while the threaded portion 21 is smaller than the notch 20 so as to be easily received therethrough and between the tips 18 and 19. The screw handle portion 22 is captured by the forked terminus 14 and seats on the beveled edge 24. In particular, the bottom of the screw handle portion 22 rests on a surface 23 which slants away from the tooth and gum region 12 as the surface 23 extends from the notch 20, and the beveled edge 24 to aid in preventing the screw 8 from slipping sidewise out of the notch 20 toward the first arm member first end 16.

The second arm member 3 is also elongate and has an operative position prior to extraction wherein same is generally parallel to and vertically spaced from the first arm member 2. The second arm member 3 has a first end 26 and an internal portion 27 located within the mouth 10.

Also in the operative position of the extractor 1, the arm member 3 has an external portion 28 thereof continuous with the internal portion 27 but located outside the mouth 10. The extent to which the first and second arm members 2 and 3 are inserted into the mouth 10 is dependent upon the position of the tooth root 9 within the mouth 10 and the size of the mouth 10.

The second arm member 3 has an inclined face 29 near the second arm first end 26 such that the arm member 3 becomes vertically narrower or flatter so as to have a thickness thereabout which is substantially less than the thickness of the external portion 28 of the second arm member 3. The second arm member 3 near the first end 26 is also horizontally somewhat wider than the external portion 28 thereof and generally oval-shaped and includes a similarly-shaped vertical aperture therethrough which defines therein an elongate oval eyelet 30. It is foreseen that the second arm member 3 near the first end 26 thereof may have various shapes, including being forked so as to allow passage of the screw 8 vertically therethrough without interference, however, being continuous, as is an oval, provides additional strength and a place on each side thereof to support the arm member 3 in a symmetrical fashion.

Preferably, the first arm member 2 has an inclined face 32 which is sloped relative to the first arm member external portion 15 and joins the latter to the forked terminus 14 so that the first and second arm members 2 and 3 form a generally mating configuration, as illustrated in FIG. 1, such that the inclined faces 29 and 32 are closely spaced when the arm members 2 and 3 are in the pre-extraction operative positions thereof. In this embodiment, the forked terminus 14 is positioned vertically from the external portion 15 of the first arm member 2 and close to the second arm member eyelet 30. The forked terminus 14 has a vertical thickness less than the remainder of the first arm member 2. The second arm member 3 is somewhat longer than the first arm member 2 so that the eyelet 30 extends further into the mouth 10 than the forked terminus 14, when the first and second arm members 2 and 3 are in the operative positions thereof and in generally mating configuration. The eyelet 30 is sized to allow unrestricted passage of the screw 8 therethrough and receipt of the screw 8 by the forked terminus 14.

A first dental saddle 34 is attached to the second arm member 3 near the first end 26 thereof. The dental saddle 34 is made of plastic, metal or a similar rigid material and is cupped to engage the tooth and gum region 12 in a stabilizing manner during the extraction procedure. Preferably, a second dental saddle 35 is positioned such that the saddles 34 and 35 are on opposite sides of the eyelet 30 and aligned with the longitudinal axis of the second arm member 3. The saddles 34 and 35 are connected to the second arm member 3 near the first end 26 thereof by threaded legs 36 and 37. The legs 36 and 37 are removably and screwably attached to the second arm member 3 by being received in vertically threaded apertures 38 and 39 respectively on opposite sides of the eyelet 30. The dental saddles 34 and 35 each include a cushion 40 and 41, respectively, constructed of rubber or a similar resilient material which absorbs sudden shock so as to allow an even force to be exerted on the tooth and gum region 12 by the second arm member 3 during the extraction procedure. It is foreseen that the dental saddles 34 and 35 are easily removable from the second arm member 3 such that various saddles having legs of different lengths (not shown) may be interchanged to accommodate varied tooth and gum regions, enabling the second arm member 3 to be placed in a generally horizontal position, for example, where teeth are on both sides of the tooth root 9. Also, it is foreseen that the saddles may be interchanged with larger or smaller saddles to accommodate larger or smaller teeth.

The eyelet 30 is positioned such that the screw 8 can be extended upwardly therethrough with sufficient clearance to allow the screw handle 22 to slide past and over the top of the forked terminus 14 when the extractor 1 is in a pre-extractor position, especially when in a slightly more closed position than just before extraction and even when the terminus 14 is spaced very close to the eyelet 30. Yet the screw 8 normally extends perpendicularly through approximately the middle of the eyelet 30 and is approximately equally spaced horizontally from the saddles 34 and 35, then the extractor 1 is in the pre-extraction position thereof. The screw 8 is preferably freely movable in the eyelet 30 without substantial abrasion from the eyelet 30 or either of the saddles 34 and 35.

The jackscrew 7 selectively manipulates the first and second arm members 2 and 3 so as to provide for selective separation between the forked terminus 14 and the eyelet 30. The jackscrew 7 is spaced from the arm member first ends 16 and 26 and from the hinge 5 so as to produce a leverage effect. In the present embodiment, the jackscrew 7 is positioned between the hinge 5 and each of the arm member first ends 16 and 26. It is foreseen that a hinge could also be positioned between spreader means and each of the arm member first ends 16 and 26, or the hinge may be eliminated if the spreader means are sufficiently stable relative to the arm members 2 and 3 to prevent substantial pivotal movement therebetween but rather only to allow vertical separation upon actuation of the spreader means.

In the present embodiment, the jackscrew 7 is spaced horizontally from the screw 8 and each of the arm member first ends 16 and 26 on one side thereof and from the hinge 5 on the other side thereof, while being pivotally secured to both arm members 2 and 3. Such placement of the jackscrew 7 provides a leverage effect to bias apart the arm member first ends 16 and 26 when pressure is exerted against the arm members 2 and 3 by the jackscrew 7, utilizing the hinge 5 as a fulcrum. The jackscrew 7 is also located externally of the mouth 10 when the extractor 1 is in the operative position thereof relative to the mouth 10 so as to be manipulated externally of the mouth 10 during the root extraction procedure.

The jackscrew 7 is operated by a disk-like knob 46 which has a circumferential periphery 47 adapted for easy manipulation. The knob 46 is coaxially attached to a pair of screw stems 48 and 49 which are oppositely threaded. The first and second arm members 2 and 3 have therein longitudinal slots 50 and 51 respectively which have threaded bushings 52 and 53 received and pivotally mounted therein. The bushings 52 and 53 threadably receive the screw stems 48 and 49, so as to operably allow the jackscrew 7 to selectively urge the first and second arm members 2 and 3 apart or together when the knob 46 is rotated. The first and second arm members 2 and 3 have opposed recesses 54 and 55 which are sized for clearance of the knob 46 when the first and second arm members 2 and 3 are urged together. The knob 46, being larger than the screw stems 48 and 49, provides purchase means for a mechanical advantage to the operator to allow extraction of a tooth root 9 with relatively less applied force than if they were the same size.

The extractor 1, as illustrated in FIG. 2, is in an exaggerated open position to show detail. In actual operation, it is not necessary for the first and second arm members 2 and 3 to be spread as far apart as FIG. 2 shows. FIG. 1 shows the extractor 1 in a closed and operative position, thereof just prior to root 9 extraction and FIG. 3 shows the extractor 1 in an open and operative position thereof just following tooth root 9 extraction.

The hinge 5 provides a pivotal connection of the arm members 2 and 3. As shown in the illustrated embodiment, the hinge 5 connects the first and second arm members 2 and 3 near respective second ends 57 and 58 thereof. The hinge 5 includes a hinge cap 59 and first and second pins 60 and 61. The hinge cap 59 is U-shaped and has an end wall 62 and two side walls 63 and 64. The first and second arm members 2 and 3 are mounted in the hinge 5 in swingable relationship relative to each other by extending the first and second pins 60 and 61 horizontally through the side walls 63 and 64 and the first and second arm members 2 and 3, respectively. Near the second ends 57 and 58 of the first and second arm members 2 and 3 are mutually diverging surfaces 65 and 66 to facilitate swinging of the first and second arm members 2 and 3 about the first and second pins 60 and 61 respectively.

In use, the tooth root screw 8 is screwed into the root channel of the tooth root 9 of a patient until snugly and tightly received therein. When emplaced within the tooth root 9, the screw 8 extends from the tooth root 9 sufficiently to allow the extractor 1 to operably engage the screw 8 in the operative position thereof.

The knob 26 of the extractor 1 is manipulated such that the arm member first ends 16 and 26 are relatively very close together and closer together than when the extractor 1 is in the just prior to extraction orientation and configuration thereof. The extractor is then is placed in the patient's mouth 10 and manipulated so that the screw 8 passes through the open part of the eyelet 30 and the screw handle 22 is vertically positioned over the forked terminus 14. Thereafter, the extractor 1 is slid horizontally until the bottom of the screw handle portion is just vertically positioned over the notch 20 of the forked terminus 14 while the upper threaded portion 21 of the screw 8 is slidably received in the notch 20, thus expediting the engagement of the screw 8 with the extractor 1 without the need for extensive mechanical adjustment. Such placement also positions the dental saddles 34 and 35 into contact with the tooth and gum region 12. The dental saddles 34 and 35 are selected and fitted both for length and size for proper engagement of the tooth and gum region 12 prior to the start of the procedure.

At this time, the knob 46 is rotated to spread or space the first arm member forked terminus 14 from the second arm member eyelet 30 so that the forked terminus 14 snugly urges the screw 8 away from the tooth root 9 and such that both are in a slightly tensed relationship. At this time the bottom of the screw handle 22 is captured in the upper beveled edge 24 of the notch 20.

Also at this time the extractor is relatively stable, as the saddles 34 and 35 push lightly against the tooth and gum region 12 and the screw 8 pulls slightly vertically against the tissue in the gum region 12 holding the tooth root 9. After this preparation, the tooth root 9 is separated from the surrounding tissue of the tooth and gum region 12 by rotating the knob 46 only a relatively small amount. Because of the leverage due to the arm members 2 and 3 being urged apart by the jackscrew 7 at a location spaced horizontally from the tooth root 9 and due to the mechanical advantage produced by the knob 46 being greater in diameter than the screw stems 48 and 49, a minimum amount of manually applied rotational force is required to extract the root 9 as compared to pulling the root 9 out without same. After the extraction has been effected, the extractor 1, with the screw 8 and tooth root 9 connected, is removed from the mouth 10 of the patient 11.

It is to be understood that while certain forms of the present invention have been illustrated and described herein, it is not to be limited to the specific forms or arrangement of parts described and shown.

What is claimed and desired to secure by Letters Patent is as follows:

1. A dental device having an operational position for extracting a tooth root from surrounding oral cavity structure; said device comprising:
   (a) first and second elongate arms connected together;
   (b) holding means positioned along said first arm near a free end thereof and adapted to operably retain a tooth root screw device secured in a tooth root;
   (c) engaging means on said second arm for bearing on the oral cavity structure surrounding the tooth rooth in such a manner as not to bear on the tooth root to be extracted; and
   (d) spreader means spaced from said holding means; said spreader means being connected to and selectively urging said first and second arms into a spaced vertical relationship at said holding means under controlled manipulation; said spreader means positioned exteriorly of the oral cavity when said dental device is in the operational position thereof.

2. A dental device for extraction of a tooth root comprising:
   (a) a first elongate arm member having a first end and a second end; said first arm member adapted to extend from a location vertically spaced from a tooth root within a mouth of a patient to a position external of the mouth;
   (b) holding means on said first arm member positioned near said first arm first end for receiving a tooth root screw connected to the tooth root to be extracted;
   (c) a second elongate arm member having a first end generally vertically spaced from said first arm first end when said device is positioned within the mouth of a patient and adapted for engaging a portion of a tooth and gum region of a patient adjacent the tooth root to be extracted;
   (d) hinge means pivotally connecting said first and second arm members and spaced from said first ends of each of said first and second arm members; and
   (e) spreader means connecting said first and second arm members and being selectively manipulative to positively urge said first end of said first and second arm members into a spaced relationship, said spreader means being spaced from said hinge means and spaced along said first and second arm members from said holding means so as to allow a user to purchase a mechanical advantage in applying force to remove the tooth root from the tooth and gum region thereof;
   (f) whereby the tooth root is urged to be vertically spaced from the tooth and gum region surrounding same when said spreader means are manipulated to space said first ends of said first and second arm members thereby extracting the tooth root.

3. A dental device for extraction of a tooth root from a surrounding tooth and gum region of a patient; said device comprising:
   (a) a tooth root screw having a functional position in a tooth root within a mouth of a patient and having a generally vertically aligned axis;
   (b) a first elongate arm member having a first end and a second end; said first arm member having an operative position wherein said first arm member extends from said screw within the mouth to a position external thereof and being aligned approximately normal to said screw axis;

(c) holding means on said first arm member for receiving said screw;

(d) a second elongate arm member having a first end and a second end; said second arm first end being generally vertically spaced from said first arm first end and adapted for engaging a portion of the tooth and gum region adjacent the tooth root to be extracted; said second arm member having an operative position wherein said second arm member is aligned with said first arm member;

(e) hinge means pivotally connecting said first and second arm members and spaced from said first ends of said first and second arm members; and (f) spreader means connecting said first and second arm members and being selectively manipulable to urge said first ends of said first and second arm members into a spaced relationship, said spreader means being spaced from said hinge means and said root screw so as to allow a user to purchase a mechanical advantage in applying force to remove the tooth root from the surrounding tooth and gum region;

(g) whereby the tooth is urged from the tooth and gum region adjacent thereto.

4. The dental device set forth in claim 3 wherein:
(a) said second arm member and said first arm member have sloped portions with respect to the horizontal, when said arm members are in the operative positions thereof, near the first ends of the respective arm member; the sloped portions slope toward the tooth and gum region of a patient; and
(b) said first arm member has a mating configuration with said second arm first end;
(c) whereby ease of in mouth manipulation of said holding means relative to said screw is facilitated while maintaining a low profile within the mouth.

5. The dental device set forth in claim 3 wherein:
(a) said holding means is located near said first arm member first end;
(b) said holding means includes a forked terminus with rounded tips and a vertical thickness less than a remaining portion of said first arm member; and
(c) said terminus includes a notch being sized to receive said screw.

6. The dental device set forth in claim 5 wherein:
(a) said terminus includes a surface vertically spaced from and opposite from the tooth and gum region of a patient when the device is operably positioned in the mouth; said surface engaging, so as to capture, an enlarged portion of said screw and being slanted away from the tooth and gum region of the patient as the surface extends away from the engagement with said screw enlarged portion to urge said screw to remain within said notch when pressure is applied to said screw by said device.

7. The dental device set forth in claim 3 wherein:
(a) said second arm member first end is generally ovalshaped and has therein an elongate oval and vertically aligned oval eyelet sized to allow passage of said screw therethrough.

8. The dental device as set forth in claim 3 which includes:
(a) a plurality of cushioned dental saddles having legs connected to said second arm member near said second arm member first end and being interchangeable and adjustable to accommodate the patient's tooth and gum region adjacent the tooth root to be extracted.

9. The dental device as set forth in claim 3 wherein:
(a) said hinge means connect said first and second arm members near said second ends thereof; and
(b) said spreader means are connected to said first and second arm members at a location horizontally spaced from both said hinge means and each of said second ends of said first and second arm members; and said spreader means are adapted to be manipulated externally of the mouth.

10. A dental device for extraction of a tooth root from an adjacent tooth and gum region of a mouth of a patient; said device comprising:
(a) a tooth root screw having a threaded portion and an enlarged handle portion; said screw having an operational position wherein said threaded portion is secured within a root channel of a tooth root within the mouth; said screw having a generally vertically aligned axis; and an extractor comprising:
(b) a first elongate arm member having a first end and a second end; said first arm member having a pre-extraction operational position wherein said first arm member extends from said screw to a location external of the mouth; said first arm member being aligned generally perpendicularly to said screw axis and having said second end thereof horizontally spaced from said screw axis;
(c) said first arm member having a forked terminus near the first end thereof operably receiving said screw; said forked terminus having a pair of tips and a thickness less than a remaining portion of said first arm member; said terminus having a vertically aligned notch between said tips and an upper chamfered periphery; said notch being sized to slidably receive said screw threaded portion but being sufficiently small to prevent passage of said screw handle portion therethrough; said terminus being slanted away from the tooth and gum region associated with the root to be extracted from said periphery to said first arm member first end so as to urge said screw to remain on said terminus when pressure is exerted against said screw by said first arm member;
(d) a second elongate arm member having a first end and a second end; said second arm member first end being generally vertically spaced from said first arm member first end and adapted for engaging a portion of the tooth and gum region adjacent the tooth root to be extracted; said second arm member having a pre-extraction operational position generally aligned with said first arm member; said second arm member sloping toward said second arm member first end so as to have a thickness less than and a width greater than a remaining portion of said second arm member; said second arm near said first end thereof being generally oval shaped and having therein an elongate and vertically aligned oval eyelet sized to allow unrestricted passage of said screw therethrough;
(e) said first arm member sloping toward said second arm member in the region of said terminus and having a mating configuration with said second arm first end so as to ease in mouth manipulation of said extractor;

(f) a plurality of cushioned dental saddles having legs connected to said second arm near the first end thereof and being interchangeable and adjustable to accommodate the tooth and gum region adjacent the tooth root to be extracted;

(g) a hinge mechanism pivotally connecting said first and second arm members near said second ends thereof; and (h) a spreader device connecting said first and second arm members and being selectively manipulable to urge said first ends of said first and second arm members into a further spaced relationship; said spreader device being substantially spaced horizontally from said screw vertical axis and from said hinge mechanism to provide a leverage effect at said first ends of said first and second arm members and being spaced to be manipulable externally of the mouth; said spreader device comprising a jackscrew pivotally connected to said first and second arm members.

11. A dental device for extraction of a tooth comprising:

(a) a tooth screw having a functional position wherein a threaded portion thereof is secured within a tooth root in a mouth of a patient;

(b) a first arm member functionally connected to said screw at a handle portion thereof and having a pre-extraction operable position relative to the tooth;

(c) a second elongate arm member being generally vertically spaced from said first arm member and adapted for engaging a portion of a tooth and gum region adjacent the tooth to be extracted; said second arm having a pre-extraction operable position generally aligned with said first arm member;

(d) hinge means pivotally connecting said first and second arm members; and (e) spreader means comprising a jackscrew pivotally connected to said first and second arm members and horizontaly spaced from said screw and said hinge means; said jackscrew being selectively manipulable to urge said screw away from the tooth and gum region associated with the tooth to be extracted so as to provide a leverage effect to facilitate extraction of the tooth.

* * * * *